(12) United States Patent
Kuiper et al.

(10) Patent No.: US 7,311,398 B2
(45) Date of Patent: Dec. 25, 2007

(54) VARIABLE FOCUS LENS

(75) Inventors: Stein Kuiper, Vught (NL); Bernardus H. W. Hendriks, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/598,258

(22) PCT Filed: Feb. 25, 2005

(86) PCT No.: PCT/IB2005/050699

§ 371 (c)(1),
(2), (4) Date: Aug. 23, 2006

(87) PCT Pub. No.: WO2005/088388

PCT Pub. Date: Sep. 22, 2005

(65) Prior Publication Data

US 2007/0153405 A1    Jul. 5, 2007

(30) Foreign Application Priority Data

Mar. 5, 2004 (GB) .................. 0404996.1
Oct. 18, 2004 (GB) .................. 0423009.0

(51) Int. Cl.
*G02C 7/06* (2006.01)
*A61F 2/16* (2006.01)

(52) U.S. Cl. .................. 351/161; 351/160 R; 359/665; 623/6.13; 623/6.27

(58) Field of Classification Search ............ 351/160 R, 351/161; 359/665; 623/6.15, 6.23
See application file for complete search history.

(56) References Cited

U.S. PATENT DOCUMENTS 5,712,721 A   1/1998   Large et al.
6,369,954 B1  4/2002   Berge et al.

FOREIGN PATENT DOCUMENTS

WO   WO0058763 A    10/2000
WO   WO2004050334 A1  6/2004

OTHER PUBLICATIONS

ISR, International Publication No. WO200088388; Pub Date Sep. 22, 2005.
B. Berge et al; "Variable Focal Lens Controlled by an External Voltage: An Application of Eletrowetting";Laboratoire De Spectrometrie Physique (UMR Universite Joseph Fourier-CNRS, 5588) B.P. 87, Eur. Phys. J.E. 3 159-163 (2000).
Gleb Vdovin et al; "On the Possibility of Intraocular Adaptive Optics"; Optics Express, vol. 11, No. 7, Apr. 7, 2003, pp. 810-817.

*Primary Examiner*—Scott J. Sugarman
*Assistant Examiner*—Darryl J. Collins
(74) *Attorney, Agent, or Firm*—Michael E. Belk

(57) ABSTRACT

A variable focus lens for an eye comprising a transparent rear wall, a transparent front wall, a cavity formed between the transparent front wall and the transparent rear wall, first and second immiscible fluids of differing refractive index contained within said cavity, and electrodes to which a voltage is able to be applied to change the curvature of a fluid meniscus between the two fluids. At least the rear wall of the lens includes a biocompatible material, which material provides for biocompatibility of the lens with the eye.

23 Claims, 4 Drawing Sheets

VARIABLE FOCUS LENS

The present invention relates to the field of variable focus lenses. The present invention has particular, but not exclusive, application to intraocular or implanted eye lenses, and to contact lenses for placement on an exterior surface of an eye.

Many people suffer from myopia. Often, as people get older they start suffering from hyperopia as well. A common solution for this problem is to wear varifocus spectacles in which the focal length of a lens changes from top to bottom. However, many people do not like wearing such spectacles, preferring instead to have separate pairs.

Naturally, it is inconvenient to need to switch between different pairs of spectacles and, clearly, the currently available varifocus lenses do not meet with universal approval. They are often found to be irritating to the user, since it may be necessary to change the way that the user views an object (e.g. tilting the head) in order to view the object through an appropriate part of the varifocus lens.

Varifocal spectacles are positioned in a region outside of a human eye. It is also possible to correct eyesight defects by using intraocular techniques.

The paper entitled 'On the possibility of intraocular adaptive optics' by Gleb Vdovin et al. in Optics Express (No.7 2003) describes the possibility to replace malfunctioning human eye lenses by adaptive eye lenses. In particular, the use of liquid crystal based lenses is proposed, since such lenses may consume very little power. Various schemes for powering or actuating the lens are discussed, for example actuation may be achieved by the use of inductive or capacitive power coupling.

However, a problem exists with the use of a liquid crystal based eye lens in that in order to have sufficiently low switching time the liquid crystal layer must be thinner than about 50 microns. This has the unfortunate drawback in that the optical power range of such a lens is constricted to about 3 dioptres. Furthermore, liquid crystal lenses may give rise to astigmatism effects when light rays enter the lens obliquely.

Finally, any corrective varifocus eye lens has material requirements in that any materials used should be biocompatible and not toxic. In the case of a liquid crystal lens this significantly limits the choice of materials available.

Clearly, an adaptive eye lens, which overcomes some or all of the above disadvantages, would be desirable.

It is noted that International patent application WO 04/050334 discloses a method of manufacturing lens elements, such as contact lenses, using a variable fluid meniscus. The lens elements which are manufactured have a fixed focal power.

It is an object of the present invention to provide a variable focus lens which is biocompatible and has a focal power which can be varied in a relatively efficient manner.

In accordance with the present invention, there is provided a variable focus lens for an eye comprising a transparent rear wall, a transparent front wall, a cavity formed between the transparent front wall and the transparent rear wall, first and second immiscible fluids of differing refractive index contained within said cavity, and electrodes to which a voltage is able to be applied to change the curvature of a fluid meniscus between the two fluids, wherein at least the rear wall of the lens includes a biocompatible material, which material provides for biocompatibility of the lens with the eye.

By changing the curvature of the fluid meniscus and by an appropriate selection of the refractive index of the first and the second fluids, light passing through the variable focus lens, via the front wall and the rear wall, can be variably focused over a relatively large range of focal powers. Operation of the lens is based upon an electrowetting principle in which the application of the voltage provides electrowetting forces which cause the meniscus to adopt a certain curvature. Variation of the voltage causes a variation of this curvature and, consequently, a variation in the focal power of the lens in a relatively efficient and simple manner.

As non-birefringent materials are used in a construction of the lens, light rays entering the variable focus lens of the present invention at an oblique angle are focused in a relatively accurate manner, in accordance with a current focal power of the lens. Consequently, the oblique light rays are not subjected to any astigmatic effects.

In a preferred embodiment of the present invention, at least one of the front wall and rear wall have a curved surface.

A curvature of the curved surface, of at least one of the front wall and the rear wall, can be selected to provide a lens with a fixed focal power which complements the focal power provided by the curvature of the fluid meniscus.

In one embodiment of the present invention the front wall and the rear wall are convex.

In a preferred embodiment of the present invention the front wall includes a biocompatible material, which material provides for biocompatibility of the lens with the eye, and the lens is adapted for implantation in a human eye.

With the front wall and the rear wall both being convex and including the biocompatible material, the variable focus lens can be implanted in a human eye in order to replace a defective human eye lens.

In one embodiment of the present invention the front wall is convex and the rear wall is concave.

In a preferred embodiment of the present invention the lens is in the form of a contact lens for placement on an exterior surface of a human eye.

With the front wall being convex and the rear wall being concave and at least the rear wall including a biocompatible material, the contact lens can be placed on an exterior surface of a human eye. In this way a defective eyesight of the human can be improved in a relatively simple manner without the need for a surgical procedure.

The implanted lens or the contact lens in accordance with embodiments of the present invention allows a human's defective eyesight to be improved such that the human can clearly view different objects requiring a different level of focal power.

In a preferred embodiment of the present invention at least one of the first fluid and the second fluid includes a biocompatible material, which material provides for biocompatibility of the lens with the eye.

The biocompatible material of any of the rear wall, the front wall, the first fluid and the second fluid is non-toxic to, and compatible with, biological tissues of the eye. When the lens is implanted in, or placed on the exterior of the eye, any complications, for example an irritation, caused by the front and/or the rear wall of the lens being in contact with tissues of the eye, are relatively minimal. Furthermore, if the first fluid and/or the second fluid leak from the lens due to, for example, an accident or an improper sealing of the lens, the biocompatibility of the fluids minimises any risk of such complications occurring if the leaking fluids make contact with the eye tissues. Should any molecules of the first and/or second fluid diffuse through the front or rear wall, any such complications are similarly minimised by the biocompatibility of the fluids.

In one embodiment of the present invention, the fluid mensicus has a contact angle with one of the front and rear walls, the contact angle determining the curvature of the fluid meniscus, and wherein at least a first of the electrodes is positioned in the lens to enable variation of the contact angle between the fluid meniscus and the wall through controlled application of the voltage, thereby altering the curvature of the fluid meniscus.

In a preferred embodiment of the present invention, the first electrode is placed on the front wall.

By placing the first electrode on the front wall of the lens, the construction of the variable focus lens is relatively compact. This allows the lens to meet necessary size criteria which allows the lens to be implanted in, or alternatively placed on the exterior surface of, the eye, without reducing the efficiency of the variation of the focus.

In a preferred embodiment of the present invention, the first and second fluids are of substantially identical specific gravity.

With the first and second fluids being of substantially identical specific gravity, the lens does not need to have a certain orientation in order to function correctly.

In a preferred embodiment of the present invention, the curvature of the fluid meniscus is varied by applying the voltage to the electrodes via one of: capacitive coupling, inductive coupling, or optical coupling.

The human can actuate and control the focus of the lens implanted in, or placed on, their eye by varying the voltage applied to the fluid meniscus. By varying the voltage using capacitive, inductive or optical coupling methods, the powering of the lens to control the focus can be performed remotely to the eye such that the human does not need to make contact with the lens of the invention itself. Additionally, the coupling methods allow control of the focus to be controlled automatically or on demand by the human, such that operation of the lens is relatively simple and efficient.

Further features and advantages of the invention will become apparent from the following description of preferred embodiments of the invention, given by way of example only, which is made with reference to the accompanying drawings.

Figure 1:
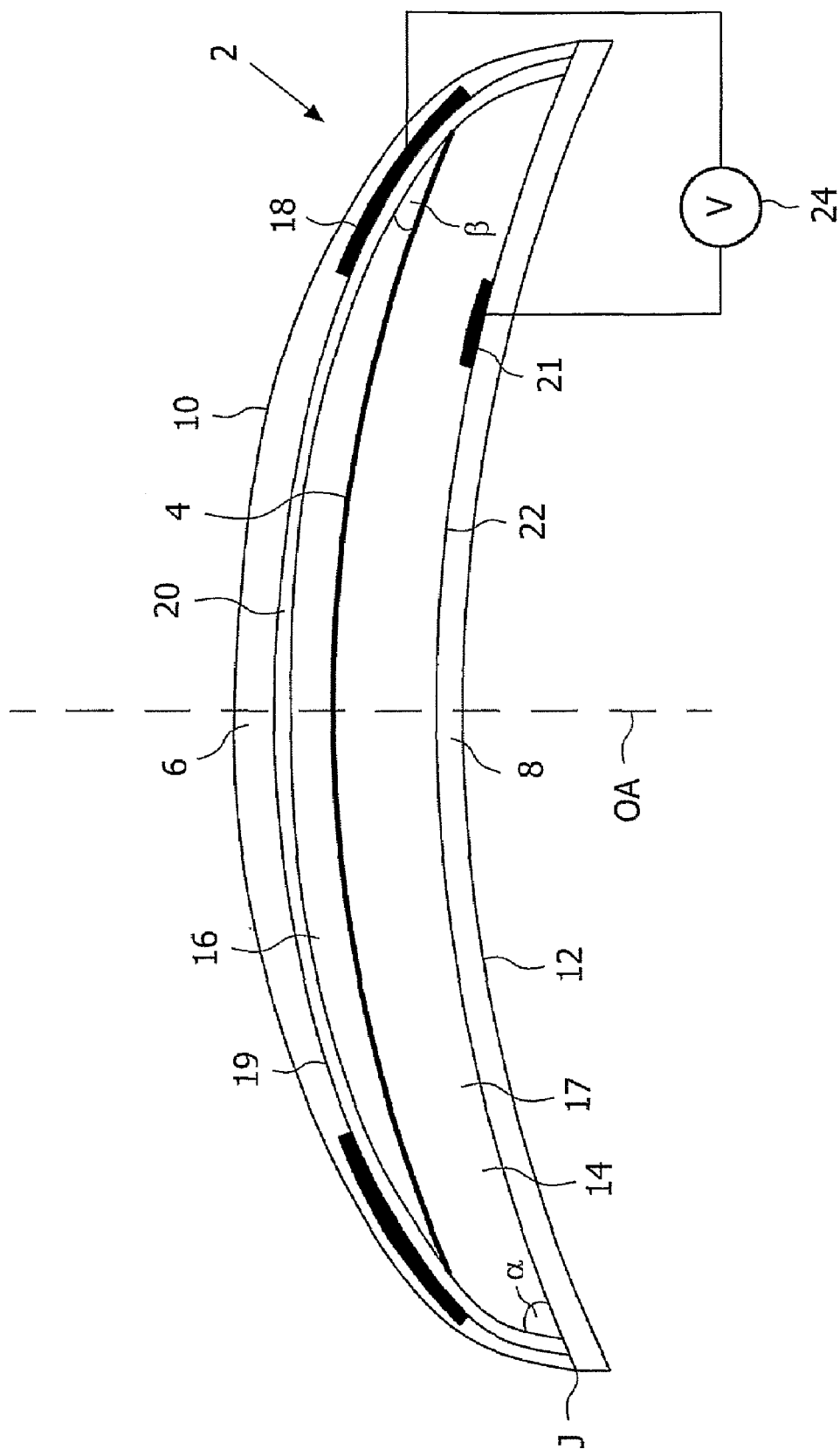
FIGS. 1 to 3 show schematically a variable focus lens having different fluid meniscus curvatures in accordance with an embodiment of the present invention.
Figure 2:
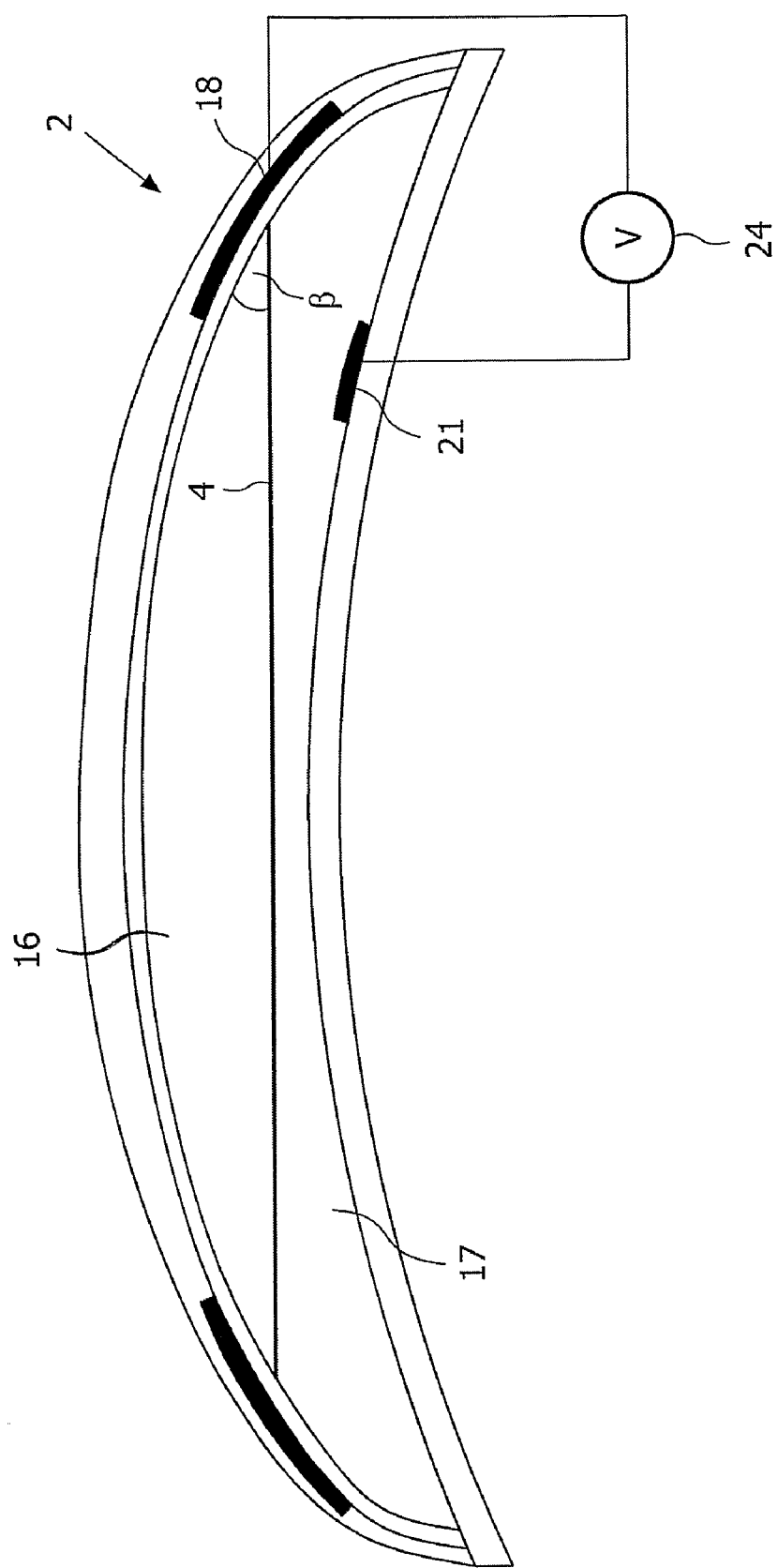
Figure 3:
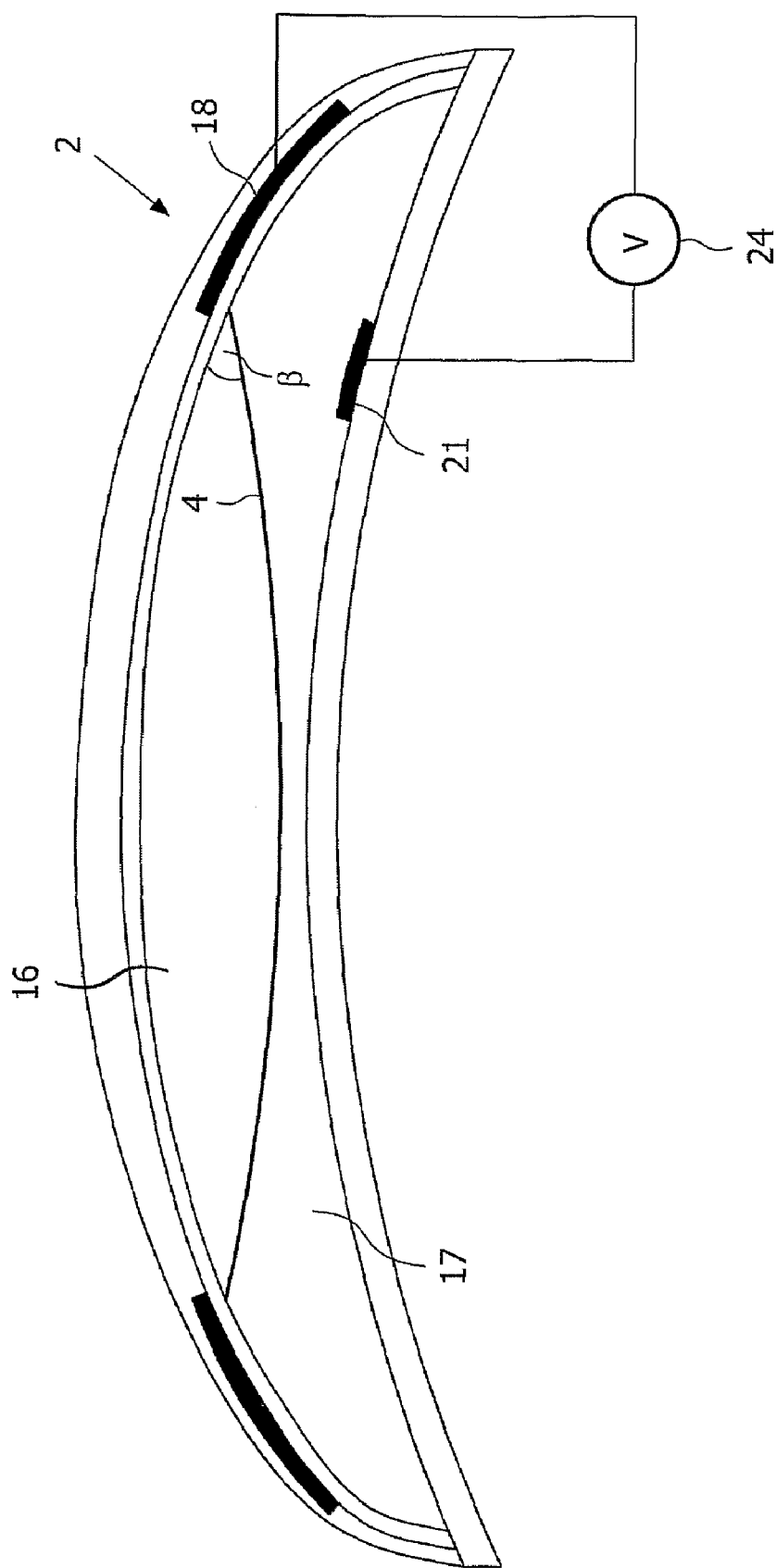

FIGS. 1 to 3 show a variable focus lens 2 in accordance with an embodiment of the present invention. FIGS. 1, 2 and 3 show, respectively, a fluid meniscus 4 of the lens 2 having a convex, planar and concave curvature, respectively. In this embodiment the variable focus lens 2 is in the form of a contact lens 2 for placement on an exterior surface of a human eye (not indicated).

Referring to FIG. 1, the lens 2 comprises a transparent front wall 6 and a transparent rear wall 8. The front wall 6 and the rear wall 8 are formed of a biocompatible material, for example polymethylmethacrylate (PMMA), a hydrogel polymer, hydroxyethylmethacrylate (HEMA), silicone rubber, a cyclic olefin copolymer (COC), or glass, which provides for biocompatibility of the lens 2 with the eye. The front wall 6 has a convex curvature such that the front wall 6 has a convex curved surface 10. The rear wall 8 has a concave curvature such that the rear wall 8 has a concave curved surface 12. The convex and the concave curvature of the front wall 6 and the rear wall 8, respectively, are rotationally symmetric about an optical axis OA of the lens 2. A thickness of the cavity between the front wall 6 and the rear wall,8 in a direction parallel the optical axis OA is greater than approximately 50 mm. The front wall and the rear walls 6, 8 each form a lens having a fixed focal power which is determined by the curvature, the refractive index of the materials and a thickness in a direction parallel the optical axis OA of the front and rear walls 6, 8. The fixed focal power is also determined by the material and refractive index of fluids in contact with the walls 6, 8. A description of these fluids follows.

A periphery of the front wall 6 and a periphery of the rear wall 8 are joined at a joining region J to form a cavity 14. At the joining region J the periphery of the front wall 6 and the periphery of the rear wall 8 form an acute internal angle α. The cavity 14 contains a first fluid 16 and a second fluid 17 which are immiscible, which each have a different refractive index and which are each formed of a material which is biocompatible with the eye. The fluid meniscus 4 lies between the first fluid 16 and the second fluid 17 so as to separate the two fluids 16, 17. In this example the first fluid 16 is a non-electrically conductive oil, for example silicone oil, which is disposed in the cavity 14 between the second fluid 17 and the front wall 6, and the second fluid 17 is an electrolyte, for example a mixture of salt and water having a low concentration, which is disposed in the cavity 14 between the first fluid 16 and the rear wall 8. In this example, the low concentration corresponds to that of a physiological (human body based) salt solution of approximately 0.9% NaCl in water. In different examples the second fluid 17 may alternatively be glycerol or diethylene glycol. In a different embodiment of the present invention it is envisaged that the first fluid is electrically conductive but is less electrically conductive than the second fluid 17.

The first and second fluid 16, 17 each have a substantially identical specific gravity. Additionally, the first and the second fluid 16, 17 each have a desired optical dispersion (indicated by a material's Abbe number), so that the contact lens 2 can improve a positive and/or a negative chromatic aberration of a defective eyesight.

A first electrode 18 is annular and is placed on the front wall 6 so as to extend around a periphery of an inner surface 19 of the front wall 6. In further embodiments of the present invention, the first electrode 18 is alternatively positioned in or in proximity to the front wall 6. The inner surface 19 is coated with a layer 20 of material, for example Teflon™AF 1600 produced by DuPont™, which is electrically insulating and hydrophobic. A second electrode 21 is placed on an inner surface 22 of the rear wall 8 and lies in direct contact with the second fluid 17. In this example the first and the second electrodes 18, 21 are both formed of a transparent and electrically conducting material such as indium tin oxide (ITO), and are electrically connected to a voltage source system 24.

The fluid meniscus 4 has a contact angle β with the front wall 6 which determines the curvature of the fluid meniscus 4. The voltage source system 24 applies a voltage to the first and the second electrode 18, 21 which determines a size of the contact angle b, and consequently the curvature of the meniscus 4. The first electrode 18 and the second electrode 21 are positioned in the lens 2 to enable variation of the size of the contact angle b through a controlled application of the voltage in order to alter the curvature of the fluid meniscus 4. In this way a focal power of the lens 2, acting upon a beam of light passing through the lens 2, can be varied. The fluid meniscus 4 is shown in FIG. 1 having a convex curvature when viewed from the front wall 6. An appropriate voltage applied to the first and second electrodes 18, 21 determines the size of the contact angle b such that the curvature is convex.

FIG. 2 shows the fluid meniscus 4 having a planar curvature. An appropriate different voltage is applied to the first and the second electrode 18, 21 such that the contact angle β is greater than that shown in FIG. 1, such that the meniscus curvature is planar.

FIG. 3 shows the fluid meniscus 4 having a concave curvature when viewed from the front wall 6. An appropriate different voltage is applied to the first and the second electrode 18, 21 such that the contact angle β is greater than that shown in FIGS. 1 and 2 such that the meniscus curvature is concave.

In a preferred embodiment it is envisaged that the meniscus 4 has a same sign of curvature as that of the cornea of the eye receiving the contact lens 2.

It is envisaged that with variation of the applied voltage, different sizes of the contact angle β can be achieved to obtain further different curvatures of the meniscus 4 to those shown using FIGS. 1 to 3.

For the embodiment of the invention described using FIGS. 1 to 3 an optically active area of the lens 2 should be of the order of the diameter of the pupil of the human eye which is approximately 8 mm or less. It is envisaged that, with the thickness of the cavity 14 being greater than approximately 50 mm and the first and second fluids 16, 17 having an appropriate refractive index, the focal power of the lens 2 can be varied between a range of positive focal powers of approximately 0 to 50 dioptres in a time of approximately 50 ms by varying the contact angle b between a maximum and a minimum size. In a different embodiment of the invention it is envisaged that the focal power of the lens 2 can alternatively be varied between a range of negative and positive focal powers of approximately −25 to +25 dioptres in a time of approximately 50 ms. In further different embodiments where the diameter of the optically active area is approximately 3 mm, it is envisaged that the focal power of the lens 2 can be varied between approximately 0 to 50 dioptres, or approximately −25 to +25 dioptres, in a time of approximately 10 ms.

A patient who wears a contact lens 2 in accordance with this embodiment can actuate and control the variable focus of the lens 2 using the voltage source system 24 in a wireless manner. Variation of the curvature of the meniscus 4 by the applied voltage occurs in a capacitive manner such that a relatively low applied voltage is required. In one embodiment of the present invention, the voltage source system 24 uses a capacitive coupling technique to remotely control the variable focus of the lens 2. In an alternative embodiment of the present invention, it is envisaged that the lens 2 includes a coil of a transparent and electrically conductive material, for example indium tin oxide (ITO), which is mounted on either of the walls 6, 8 of the lens 2, or on a circumference of the lens 2. The patient can use a control unit (not indicated) to wirelessly supply power and control the variable focus of the lens 2 by an inductive coupling technique. In a yet further envisaged embodiment of the present invention, the voltage source system 24 includes a photocell (not indicated) and the patient can use a control unit (not indicated) to wirelessly supply power and control the variable focus of the lens 2 by optical coupling, using for example infrared electromagnetic radiation.

In further embodiments of the invention, it is envisaged that triggering the change in focal power of the lens 2 by the patient is accomplished relatively simply by the provision of a control unit comprising a power unit and a button on, for example, an "empty" spectacle frame. Alternatively, it is envisaged that the patient controls the variation of focal power of the lens 2 using a pattern of blinks. In a further embodiment of the invention, it is envisaged that an inclusion of distance measuring apparatus enables an automatic focusing system to be provided to the patient.

Further details of a voltage source system utilising capacitive, inductive and optical coupling techniques are included herein by way of the following reference: 'On the possibility of intraocular adaptive optics' by Gleb Vdovin et al. in Optics Express (No.7 2003).

By controlling the focal length of the lens 2, the lens 2 is particularly useful to users with both short and long distance eyesight correction requirements. Changing the focal length of the lens 2 could, for example, be used to change between a focal length suitable for distance vision and a focal length suitable for reading vision.

The choice of materials for the front and rear walls 6, 8 can be chosen to achieve a hard type of contact lens (plastic housing) or a soft lens arrangement of contact lens. The curvature of the front and rear walls should be chosen so as to mimic the curvature and size of a patients eyeball.

It is envisaged that the material of the rear wall 8 may be permeable to oxygen to aid the "breathing" requirements of the eyeball, whilst in such cases interior surfaces of the cavity 14 should be coated with an impermeable coating to retain the integrity of the lens and to contain the first fluid and the second fluid 16, 17.

Optionally, it may be possible to use oxygen permeable materials to form the front and rear walls 6, 8 if fluids having long-chained molecules are used for the first and the second fluid 16, 17. Hence, the construction of a variable focus, semi permeable contact lens is enabled.

Figure 4:
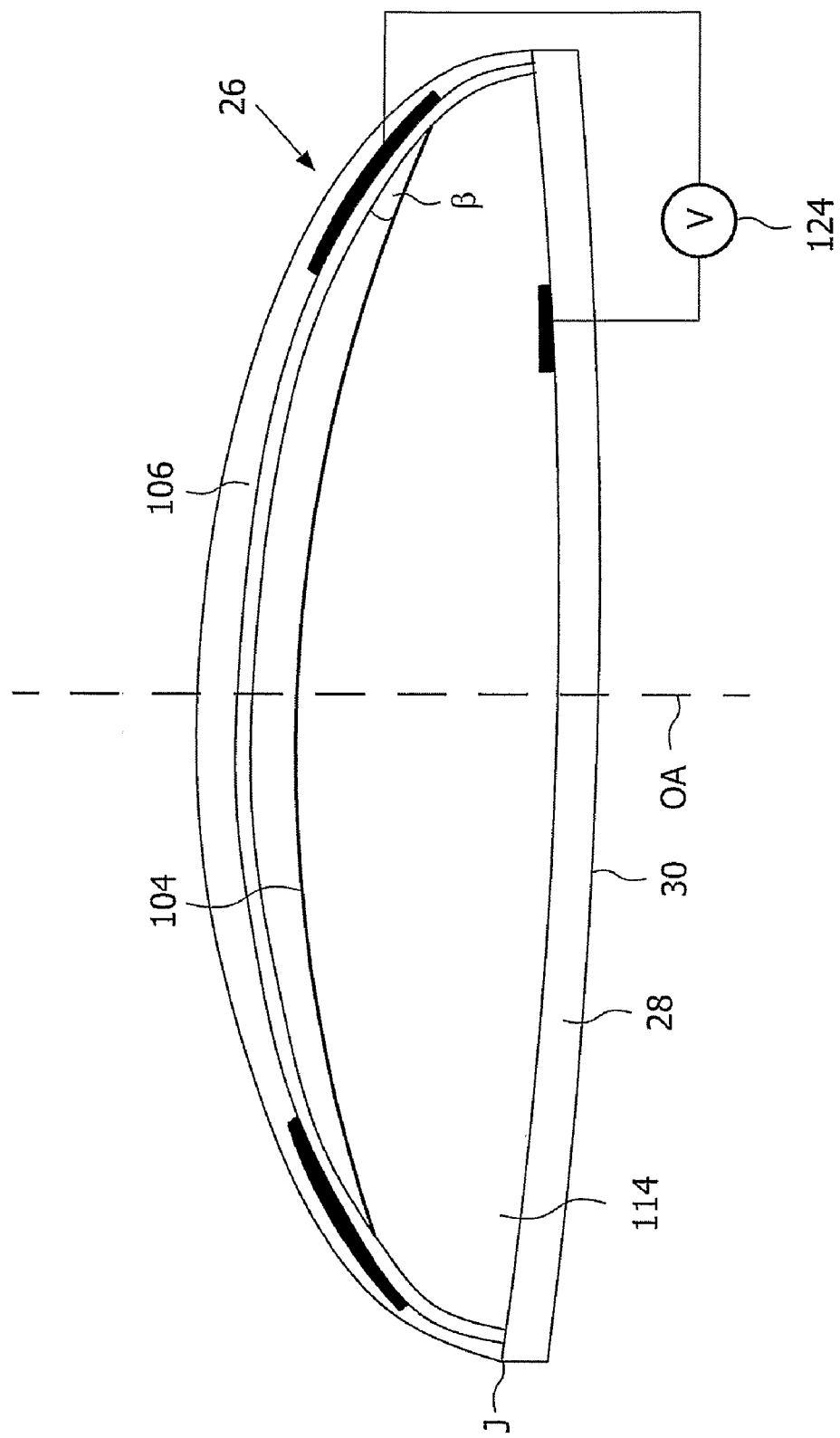
FIG. 4 shows schematically a variable focus lens in accordance with a different embodiment of the present invention.

FIG. 4 shows a variable focus lens 26 in accordance with a different embodiment of the present invention. In this embodiment the variable focus lens 26 is adapted for implantation in a human eye (not indicated). Elements and features of the lens 26 are similar to elements and features of the lens described previously using FIGS. 1 to 3 and are referenced using the same reference numerals, incremented by 100. Similar descriptions should be taken to apply here also.

A periphery of the front wall 106 is joined at a joining region J to a periphery of a rear wall 28. The rear wall 28 has a convex curvature such that the rear wall has a convex curved surface 30. The convex curvature of the rear wall 28 is rotationally symmetric about the optical axis OA of the lens 26. A thickness of the cavity 114 between the front wall 106 and the rear wall 28 in a direction parallel the optical axis OA is greater than approximately 50 mm. Both the front wall 106 and the rear wall 28 are formed of a transparent material which is biocompatible with the eye. This biocompatible material is, for example, one of the biocompatible materials detailed for the embodiment described previously using FIGS. 1 to 3.

In this example, preferably the size of the lens 26 corresponds approximately with that of the human eye lens itself. Hence a diameter of the lens 26 is approximately 10 mm and a total thickness, in a direction parallel the optical axis OA, of the lens 26 is approximately 4 mm. Additionally, as the human eye provides a positive focus, the lens 26 of this embodiment preferably provides only a positive focal power.

The lens 26 is implanted in a human eye using a surgical technique where a human eye lens, which, for example has a cataract, is removed, via an incision in the eye, and replaced with the variable focus lens 26 of this embodiment.

Once the lens 26 is implanted, the curvature of the meniscus 104 can be varied using the voltage source 124 to obtain convex, planar and concave meniscus curvatures when viewed from the front wall 106, in a similar manner to that described previously. FIG. 4 shows the fluid meniscus 4 having a convex curvature when viewed from the front wall 106.

The above embodiments are to be understood as illustrative examples of the invention. Further embodiments of the invention are envisaged.

In the described embodiments, fluids having certain refractive indices and optical dispersion values are detailed. It is envisaged that in further embodiments of the present invention fluids having different of such values may be used and may be fluids of a different material to those described previously. Furthermore, a thickness of the cavity, dimensions and shapes of features of the lens, curvatures of the walls and certain focal powers which can be achieved by the lens, have been detailed. It is envisaged that in further embodiments of the invention the lens may have a different thickness of the cavity, that the dimensions or shapes of features of the lens and curvatures of the walls, are different, and that different focal powers may be achieved.

As described above, the fluid meniscus forms a contact angle with the front wall. It is envisaged that in further embodiments the meniscus may alternatively form a contact angle with the rear wall. In further alternative embodiments the first fluid is disposed between the rear wall and the meniscus and the second fluid is disposed between the front wall and the meniscus. The arrangement of the fluids may determine whether the lens provides a positive or a negative focal power.

From reading the present disclosure, other modifications will be apparent to persons skilled in the art. Such modifications may involve other features which are already known in the design, manufacture and use of variable focus lenses and component parts thereof, and which may be used instead of or in addition to features already described herein.

The invention claimed is:

1. A variable focus lens (2; 26) for an eye comprising a transparent rear wall (8; 28), a transparent front wall (6; 106), a cavity (14; 114) formed between the transparent front wall and the transparent rear wall, first and second immiscible fluids (16, 17) of differing refractive index contained within said cavity, and electrodes (18, 21) to which a voltage is able to be applied to change the curvature of a fluid meniscus (4; 104) between the two fluids, wherein at least the rear wall of the lens includes a biocompatible material, which material provides for biocompatibility of the lens with the eye.

2. A variable focus lens according to claim 1, wherein at least one of the front wall and rear wall have a curved surface (10, 12; 30).

3. A variable focus lens according to claim 2, wherein the front wall and the rear wall are convex.

4. A variable focus lens according to claim 1, wherein the front wall includes a biocompatible material, which material provides for biocompatibility of the lens with the eye, and the lens (26) is adapted for implantation in a human eye.

5. A variable focus lens according to claim 2, wherein the front wall is convex and the rear wall is concave.

6. A variable focus lens according to claim 5, wherein the lens is in the form of a contact lens (2) for placement on an exterior surface of a human eye.

7. A variable focus lens according to claim 1, wherein the fluid meniscus has a contact angle (β) with one of the front and rear walls, the contact angle determining the curvature of the fluid meniscus, and wherein at least a first of the electrodes (18) is positioned in the lens to enable variation of the contact angle between the fluid meniscus and the wall through controlled application of the voltage, thereby altering the curvature of the fluid meniscus.

8. A variable focus lens according to claim 7, wherein the first electrode is positioned in or in proximity to the wall with which the fluid meniscus has a contact angle.

9. A variable focus lens according to claim 7, wherein the first electrode is annular and is placed to extend around the periphery of an inner surface of the wall with which the fluid meniscus has a contact angle.

10. A variable focus lens according to claim 1, wherein the first electrode is placed on the front wall.

11. A variable focus lens according to claim 1, wherein the distance between the front wall and rear wall is greater than 50 microns.

12. A variable focus lens according to claim 1, wherein the distance between the front wall and rear wall is such that an optical power of the lens can be varied between 0 and 50 dioptres by altering the curvature of the fluid meniscus.

13. A variable focus lens according to claim 1, wherein the distance between the front wall and rear wall is such that an optical power of the lens can be varied between −25 and +25 dioptres by altering the curvature of the fluid meniscus.

14. A variable focus lens according to claim 1, wherein a periphery of the front wall joins a periphery of the rear wall to form an acute internal angle (□) at their joining region (J).

15. A variable focus lens according to claim 1, wherein the first and second fluids are of substantially identical specific gravity.

16. A variable focus lens according to claim 1, wherein at least one of the first fluid and the second fluid includes a biocompatible material, which material provides for biocompatibility of the lens with the eye.

17. A variable focus lens according to claim 1, wherein the first and second fluids are oil and an electrolyte respectively.

18. A variable focus lens according to claim 17, wherein the oil is disposed in the cavity between the electrolyte and the front transparent wall, and the electrolyte is disposed in the cavity between the oil and the rear transparent wall.

19. A variable focus lens according to claim 17, wherein the electrolyte is disposed in the cavity between the oil and the front transparent wall, and the oil is disposed in the cavity between the electrolyte and the rear transparent wall.

20. A variable focus lens according to claim 17, wherein the electrolyte comprises a water/salt mixture.

21. A variable focus lens according to claim 1, wherein the first fluid is less conductive than the second fluid.

22. A variable focus lens according to claim 1, wherein the biocompatible material is polymethylmethacrylate (PMMA), a hydrogel polymer, hydroxyethylmethacrylate (HEMA), silicone rubber, a cyclic olefin copolymer (COC), or glass.

23. A variable focus lens according to claim 1, wherein the curvature of the fluid meniscus is varied by applying the voltage to the electrodes via one of:
  capacitive coupling, inductive coupling, or optical coupling.

* * * * *